United States Patent
Beek et al.

(10) Patent No.: US 9,562,114 B2
(45) Date of Patent: Feb. 7, 2017

(54) CYCLIC CARBONATE AZIDE

(71) Applicant: Akzo Nobel Chemicals International B.V., Arnhem (NL)

(72) Inventors: Waldo Joseph Elisabeth Beek, Deventer (NL); Auke Gerardus Talma, Bathmen (NL)

(73) Assignee: AKZO NOBEL CHEMICALS INTERNATIONAL B.V., Arnhem (NL)

( * ) Notice: Subject to any disclaimer, the term of this patent is extended or adjusted under 35 U.S.C. 154(b) by 0 days.

(21) Appl. No.: 15/035,008

(22) PCT Filed: Oct. 31, 2014

(86) PCT No.: PCT/EP2014/073417
§ 371 (c)(1),
(2) Date: May 6, 2016

(87) PCT Pub. No.: WO2015/067532
PCT Pub. Date: May 14, 2015

(65) Prior Publication Data
US 2016/0280805 A1  Sep. 29, 2016

(30) Foreign Application Priority Data
Nov. 7, 2013 (EP) ..................... 13191971

(51) Int. Cl.
C07D 317/34 (2006.01)
C08C 19/22 (2006.01)
C08K 3/36 (2006.01)

(52) U.S. Cl.
CPC ............. *C08C 19/22* (2013.01); *C07D 317/34* (2013.01); *C08K 3/36* (2013.01)

(58) Field of Classification Search
CPC .......... C08C 19/22; C07D 317/34; C08K 3/36
USPC ......................... 549/221; 524/572
See application file for complete search history.

(56) References Cited

U.S. PATENT DOCUMENTS

| | | |
|---|---|---|
| 3,205,206 A | 9/1965 | Marcantonio et al. |
| 3,631,182 A | 12/1971 | Breslow |
| 4,287,294 A | 9/1981 | Rubner et al. |
| 4,329,556 A | 5/1982 | Rubner et al. |
| 4,352,938 A | 10/1982 | Breslow |
| 6,313,314 B1 | 11/2001 | Cheng et al. |
| 9,388,276 B2 * | 7/2016 | Song ...................... A61L 27/18 |

FOREIGN PATENT DOCUMENTS

| | | |
|---|---|---|
| EP | 0019122 A2 | 11/1980 |
| EP | 0019726 A1 | 12/1980 |
| EP | 0143380 A2 | 6/1985 |
| JP | 4372662 B2 | 11/2009 |
| WO | 2012/116250 A1 | 8/2012 |

OTHER PUBLICATIONS

Stuart A. Bateman, et al., "Sulfonyl Azides—An Alternative Route to Polyolefin Modification," Journal of Applied Polymer Science, vol. 84, (2002), pp. 1395-1402.
A.J. Zielinska, Cross-Linking and Modification of Saturated Elastomers Using Functionalized Azides, Dissertation, University of Twente, Jul. 1, 2011 (1 of 2, cover page to p. 78).
A.J. Zielinska, Cross-Linking and Modification of Saturated Elastomers Using Functionalized Azides, Dissertation, University of Twente, Jul. 1, 2011 (2 of 2, pp. 79-165).
Anon, Research Disclosure (1999), 427 (Nov.), P-1472 (No. 427060).
J.E. Mark et al., The Science and Technology of Rubber, Third Edition, 2005, pp. 388-391.
Elisa Passaglia et al., "Effect of Structure of Functionalizing Molecules on the Inter-Macromolecular Reactions and Blending of Poly(ethylene-co-propylene) (EPM) With Poly (6-aminohexanoic Acid) (PA6)", Helvetica Chimica ACTA, vol. 89, No. 8, Aug. 30, 2006, pp. 1596-1609.

(Continued)

*Primary Examiner* — Kelechi Egwim
(74) *Attorney, Agent, or Firm* — Alice C. Su

(57) ABSTRACT

Cyclic carbonate azide having a structure according to the following formula (A) wherein $R^1$-$R^5$ are independently selected from the group consisting of hydrogen, $C_{6-20}$ aryl, $C_{7-36}$ aralkyl, and $C_{1-30}$ alkyl groups; said aryl, aralkyl, and alkyl groups my optionally be substituted with heteroatoms, X is a hydrocarbon moiety having at least one carbon atom, T has the structure —N($R^6$)— or —O—, $R^6$ is selected from the group consisting of hydrogen and $C_{1-20}$ alkyl groups, optionally substituted with heteroatoms, k is 0, 1, or 2, m is 0 or 1, n is 0 or 1, p is 1 or 2, Z is an aliphatic or aromatic hydrocarbon moiety having at least one carbon atom, optionally substituted with heteroatoms, and Y is either (B) or C) or (D).

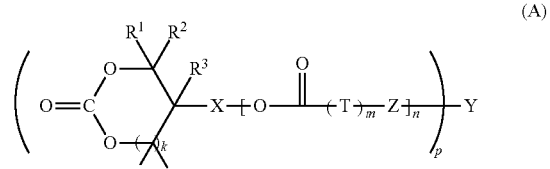

(A)

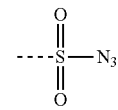

(B)

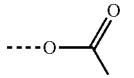

(C)

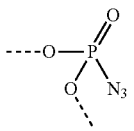

(D)

17 Claims, No Drawings

(56) References Cited

OTHER PUBLICATIONS

J.K. Jorgensen et al., "Introduction of Long-Chain Branches in Linear Polyethylene by Light Crosslinking with 1,3-Benzenedisulfonyl Azide," Polymer, 46, (2005), pp. 12256-12266.

* cited by examiner

CYCLIC CARBONATE AZIDE

This application is a national stage filing under 35 U.S.C. §371 of PCT/EP2014/073417, filed Oct. 31, 2014, which claims priority European Patent Application No. 13191971.4, filed Nov. 7, 2013, the contents of which are each incorporated herein by reference in their entireties.

The present invention relates to new azide compounds having a cyclic carbonate functionality. The invention also relates to their use for the modification of polymers.

Polymers such as elastomers are known to be very apolar. This apolarity limits the uptake of polar compounds, such as fillers, and limits the resistance towards swell in apolar compounds like oils and fuels.

Modification of polymers to enhance polymer-filler interaction is currently done during the polymerization reaction by building in functionalized monomers. A drawback of this in situ modification is that the functional groups that are present during the polymerization affect the entire polymerization system, leading to different molecular weights and branching levels compared to the complementary non-functionalized polymers. Another drawback of this in situ approach is that the level of functionality cannot be changed.

It is therefore an object of the present invention to provide a process for the modification of a polymer via an ex situ process, i.e. after preparation of the desired polymer. This allows for the modification of a broader spectrum of polymers and different levels of modification. This will give compounders more degrees of freedom to select the materials of choice and to optimize the level of functionality to their needs.

Modification of polymers with functionalized azides is know from U.S. Pat. No. 4,352,938. This document discloses the modification of polymers with an epoxy-azidoformate in order to improve the bonding between the polymer and a substrate.

A disadvantage of epoxy functionalities is their poor interaction with polar surfaces; for instance of fillers and substrates. For the manufacture of truck tread compounds based on epoxy modified natural rubber (ENR), modification levels of >25% or even 50% epoxide are required. Another disadvantage of epoxies is their tendency towards self-polymerization, which leads to rigid structures. Furthermore, epoxy-functional resins are conventionally hardened with amines, which have the tendency to react with more than one epoxy-group—even in the case of mono-amines— which leads to premature crosslinking. In addition, epoxy-amine crosslinks are rather inflexible.

In so-called green tires (category A label tires), silica is used as a reinforcing filler to enhance properties like wet grip and rolling resistance in order to arrive at low fuel consumption, low noise generation, and durable safe tires. The interaction between the silica filler and the rubber is critical. In these green tire recipes, epoxidised rubbers cannot be used because of their difficulty in processing. Instead, the rubber-silica interaction is improved by additives such as Si69-bis(triethoxysilylpropyl)tetrasulfide: a bifunctional, sulfur-containing organosilane. These additives are added during the compounding of the silica into the rubber in amounts of 5-10 parts per 100 rubber (phr).

There are several recognized disadvantages of this approach. First of all, the organosilane reacts with the hydroxy groups on the silica surface during the compounding step via a so-called silanization reaction. This leads to the release of volatiles like ethanol (in case of Si69), or even methanol (in case of other silanes). Secondly, the high reactivity between the organosilane and the silica surface leads to processing problems during and after mixing the silica into the rubber. This makes processing of the compounds tedious and only very skilled people can make these green tire compounds. And finally, the silanization reaction is assisted by an accelerator called DPG (diphenyl guanidine), which is considered to be toxic because it releases aniline (a Group III carcinogen) and may face use restrictions in the near future.

A preferred type of polymer to be used in green tires is SBR (styrene-butadiene rubber). There are two main types of SBR: solution-type SBR (s-SBR)-a polymer prepared by an anionic living polymerization reaction between styrene and butadiene- and emulsion-type SBR (e-SBR)-a polymer prepared by a radical polymerization between styrene and butadiene.

The interaction between s-SBR and silica can be improved by building in functionalities during the polymerization, which is called reactor modification. Such modified sSBR grades are, however, not widely available and accessible. A further disadvantage of this reactor modification of s-SBR is that it does not allow a compounder or tire manufacturer to design the compound recipe according its needs.

E-SBR is generally regarded as not modifiable in terms of structure and functionality.

It is therefore the object of the present invention to provide a process for modifying a polymer to improve the polymer-filler interaction while allowing a compounder or tire manufacturer to design the compound recipe according its needs and without the requirement of silanizing silica surfaces.

A further object is to provide a method for modifying e-SBR.

These objects are achieved by modifying polymers with a new compound: a cyclic carbonate azide.

The present invention therefore relates to a cyclic carbonate azide having a structure according to the following formula:

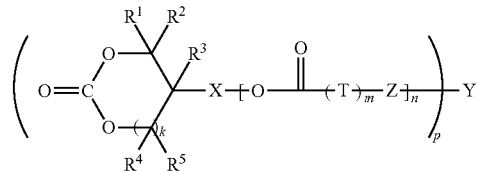

wherein $R^1$-$R^5$ are independently selected from the group consisting of hydrogen, $C_{6-20}$ aryl, $C_{7-36}$ aralkyl, and $C_{1-30}$ alkyl groups; said aryl, aralkyl, and alkyl groups my optionally be substituted with heteroatoms, X is a hydrocarbon moiety having at least one carbon atom, T has the structure —N($R^6$)— or —O—, $R^6$ is selected from the group consisting of hydrogen and $C_{1-20}$ alkyl groups, optionally substituted with heteroatoms k is 0, 1, or 2 m is 0 or 1, n is 0 or 1, p is 1 or 2

Z is an aliphatic or aromatic hydrocarbon moiety having at least one carbon atom, optionally substituted with heteroatoms, and Y is either

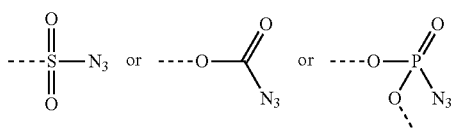

The invention also relates to the use of this azide for the modification of a polymer. A polymer modified with this azide will have an increased polarity and this will lead to an enhanced interaction with polar groups on fillers like silica, carbon black, and clays. It can also enhance the compatibility of a non-polar functionalized polymer with polar polymers like ethylene-vinyl acetate (EVA), (hydrogenated) nitrilbutadiene rubber, and polyamides (such as PA66 type polyamides), etc. It may also improve the interaction with subsequent paint layers and even lead to an improvement in rheology (e.g. melt flow, melt strength) of the polymer.

Like epoxy-functional resins, cyclic carbonate-functional polymers are also cured with amines. Cyclic carbonates are known to react only with primary amines and are therefore more selective in the reaction with amines. A clear advantage of this is that during processing of modified polymers with amine curatives there is an increased scorch (onset of cure) time when compared to epoxies. An additional advantage is that the more selective reactivity of the cyclic carbonates leads to better defined reaction products: the reaction product cannot react further, which allows for a selective functionalization. Furthermore, reaction with bis- and polyamines results in the formation of more flexible crosslinks when compared to epoxy-amine bridges.

In the above structure of the cyclic carbonate azide, X is most preferably a methylene group, i.e. $CH_2$.

In the above structure of the cyclic carbonate azide, k is preferably 0 or 1; most preferably 0.

$R^1$ in the cyclic carbonate azide structure is most preferably hydrogen.

$R^2$ in the cyclic carbonate azide is most preferably hydrogen.

If $k \neq 0$ and the cyclic carbonate azide thus contains an $R^4$ and an $R^5$ group, these groups are most preferably hydrogen.

$R^3$ is preferably selected from hydrogen, alkyl groups, and hydroxyl alkyl groups (i.e. —$C_xH_{2x}OH$), more preferably H, —$CH_3$, —$C_2H_5$, or —$CH_2OH$, and most preferably H.

In a more preferred embodiment, p=1, n=m=0, and Y is:

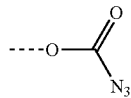

A particularly preferred example of such a compound is (2-oxo-1,3-dioxolan-4-yl)methyl carbonazide; in which k=0, X is $CH_2$, and $R^1=R^2=R^3=H$ In yet another more preferred embodiment, p=1, n=m=1, T=—N(H)—, Z is an aryl group, and Y is

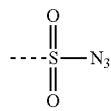

A particularly preferred example of such a compound is 4-(azidosulfonyl)phenyl ((2-oxo-1,3-dioxolan-4-yl)methyl) carbonate; in which k=0, X is $CH_2$, and, $R^1=R^2=R^3=H$.

In another more preferred embodiment, p=1, n=m=1, T=—O—, Z is an aryl group, and Y is

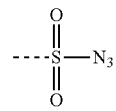

A particularly preferred example of such a compound is 4-(azidosulfonyl)phenyl((2-oxo-1,3-dioxolan-4-yl)methyl) carbonate; in which k=0, X is $CH_2$, and, $R^1=R^2=R^3=H$ In a further embodiment, p=2, n=m=0 and Y is:

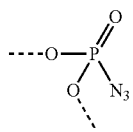

A particularly preferred example of such compound is a compound wherein k=0, X is $CH_2$, and $R^1=R^2=R^3=H$.

In another embodiment, k=1, $R^1=R^2=R^4=R^5=H$, and $R^3$ is an alkyl group, most preferably —$C_2H_5$.

The cyclic carbonate azide according to the present invention can be prepared by reacting a diol or triol, e.g. glycerol or 1,2-glycol, with dimethylcarbonate or carbon dioxide, followed by a reaction of the resulting product with either i) trifosgene to form a chloroformate and with sodiumazide to make the azidoformate, ii) trifosgene to form the chloroformate and with azides that have functionalities (e.g. amines) that react with chloroformates, iii) trifosgene to make the chloroformate followed by reaction with a molecule that has a functionality that can react with chloroformates and has a functionality that can be reacted in a further step into an azide, iv) an isocyanate-functionalized azide, or v) an isocyanate-functionalized molecule with an additional functionality that can be converted into an azide in a further step. Also reverse procedures are possible where the azide-part is prepared first and the cyclic carbonate is produced at a later stage.

The cyclic carbonate azide according to the present invention can be used to modify polymers. The azide functionality reacts with the polymer, thereby providing a functionality on the polymer chain. An azide has several modes in which it can react with polymers, depending on the type of azide and the type of polymer. Azides generally decompose thermally into two types of nitrenes: singlet (majority) and triplet (minority). A reaction of the singlet state of the nitrene with a fully saturated polymer chain (like EPM) gives insertion of the azide into the polymer chain (grafting). Reaction of singlet and triplet nitrene with unsaturated polymers like SBR results into addition reactions onto double carbon-carbon bonds which also leads to grafting. In unsaturated polymers and polymers with unsaturated moieties, one additional reaction also occurs: the insertion of the azide into double bonds before the decomposition of the azide into nitrenes. This insertion generally occurs at lower temperatures than the decomposition temperature of the azide into the nitrene and is generally referred to as "click" reaction. In general, no volatiles other than nitrogen are released by these grafting steps.

The modification can be performed by blending the polymer and the azide at temperatures ranging from 100 to 220° C., depending on the type of azide and polymer used. Blending can be performed in different ways, including melt-blending, mixing in two roll mills, extrusion, mixing from a common solvent, etc. It is also possible to mix the azide into a compounded polymer, i.e. a polymer already blended with oils, fillers, and other optional additives such as antidegradants, colorants, etc.

In a preferred embodiment, an anti-oxidant is present during the grafting step. The anti-oxidant helps to prevent premature gel formation. Examples of suitable anti-oxidants are sterically hindered polynuclear phenols (e.g. Vulkanox® SKF, Vulkanox® DS, Vulkanox® BKF, Irganox® 1010), aminic antioxidants (e.g. Flectol® TMQ), diphenyl diamin-based antioxidants (e.g. Santonox® 6PPD), and phosphites (e.g. Weston TNPP). The anti-oxidant is preferably present during the grafting step in an amount of 0-5 phr (=weight parts per hundred weight parts of rubber), more preferably 0.1-3 phr, and most preferably 0.5-2.5 phr.

After modification, the polymer contains polar groups that (i) improve the interaction with fillers, (ii) improve the resistance to swell in apolar solvents like oils and fuels, and/or (iii) are reactive towards several different chemicals, e.g. di-, tri- or polyamines, di-, tri- or polythiols, di-, tri- or polyols and di-, tri- or polymeric acids. The reactivity towards several different chemicals allows crosslinking of the modified polymers by other methods than the conventional peroxide or sulfur-cure processes.

Examples of polymers that can be modified in this way include chain saturated polymers such as polyolefins like polyethylene and polypropylene, ethylene-propylene copolymers (EPM), polyolefin elastomers like ethylene octene copolymers (POE), ethylene-propylene-diene copolymers (EPDM), hydrogenated nitrile rubber (HNBR), and ethylene vinylacetate copolymers (EVA); unsaturated polymers like styrene-butadiene copolymers (SBR), natural rubber (NR), isoprene rubber (IR), polybutadiene rubber (BR), nitrile rubber (NBR), and latexes of NR, IR and SBR. Other polymers that can be modified this way are polyesters, including both saturated and unsaturated polyesters, for example for use in coatings, powder coatings and thermoset resins.

Preferred types of polymer to be modified are s-SBR and e-SBR. The process according to the present invention allows for post-reactor modification of these rubbers, a better interaction between these rubbers and fillers like silica, and crosslinking of said rubbers with bisamines.

As explained above, a good interaction between silica and e-SBR or s-SBR is essential for the use of SBR in so-called "green tires", in which the combination of silica and SBR is used to optimize tire properties like wet-grip and low rolling resistance. Presently, such interaction is only achieved by using a specific solution-type SBR in combination with silica that has been surface-modified. The present invention now allows for the use of e-SBR and standard s-SBR with unmodified silica.

The ability of crosslinking SBR with difunctional amines allows crosslinking without peroxides or sulfur/sulfur-accelerator systems and can be performed volatile-free. Amine crosslinking of cyclic carbonate-modified SBR can be performed using bis- or polyamines at elevated temperatures: 100-180° C. At lower temperatures the reactivity of amines versus cyclic carbonates is not high enough. During crosslinking, the bis- or polyamines are built-in into the network and thereby contribute to the mechanical properties of the crosslinked polymer. Other crosslinking systems that are very similar utilize thiol, alcohol or acid functionalities instead of amines. Reactions with acids and alcohols are base-catalyzed. Reaction of cyclic carbonates with amines and thiols is typically performed at lower temperatures than the reaction with alcohols and acids.

EXAMPLES

Example 1

Preparation of (2-oxo-1,3-dioxolan-4-yl)methyl carbonazide

A mixture of 26 gram trifosgene and 18 gram sodium carbonate in 70 ml THF was cooled to 0° C. and stirred at this temperature for 30 minutes. After that, 20 gram of 4-(hydroxymethyl)-1,3-dioxolan-2-one in 70 ml THF was added slowly over a period of 30 minutes. The reaction mixture was stirred at room temperature during the night. The formed salt was removed by filtration and the solvent was removed under reduced pressure to result in 27 gram of a colorless oil being technically pure 2-oxo-1,3-dioxolan-4-yl)methyl carbonochloridate.

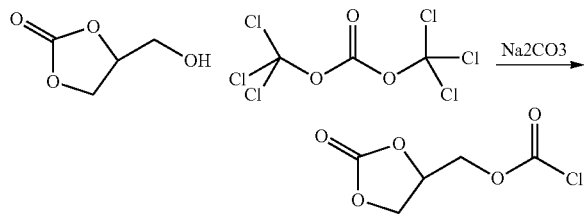

2-oxo-1,3-dioxolan-4-yl)methyl carbonochloridate (2 g, 11.08 mmol) was dissolved in 7 ml acetone and cooled to −10° C. A solution of 0.791 g sodium azide in 8 ml water was added dropwise to this cooled solution in 15 min. The mixture was stirred for 2 hours at a temperature between 0 and −10° C. A white solid was formed. Ice-water (50 g) was added to the mixture and the white solid was filtered, washed with water, and dried in air, yielding 1 gram of the cyclic carbonate azide:

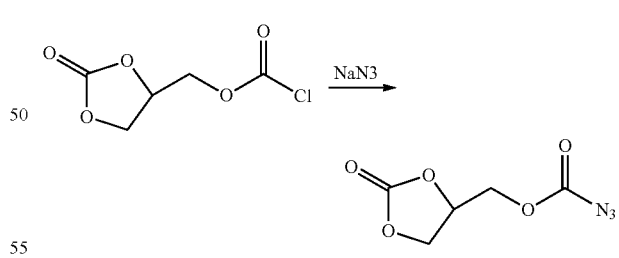

Example 2

Preparation of (2-oxo-1,3-dioxolan-4-yl)methyl (4-azidosulfonyl)phenyl)carbamate 40.0 g 4-acetamidobenzenesulfonyl azide (ex Sigma Aldrich) was dissolved in 160 ml concentrated hydrochloric acid. The solution was stirred and heated to 80° C. for a maximum of 30 min. The clear solution was cooled to room temperature. At 70° C., a precipitate formed. The cooled mixture was added to ice-water (200 g) in order to dissolve all components and the resulting solution was added to 1000 gram of a 20% aqueous sodium carbonate solution. The product was extracted twice with 150 ml dichloromethane and the combined extracts were dried over sodium sulfate, filtered and concentrated in vacuum, and finally dried in air to remove all volatiles. This resulted in 30 gram of solid 4-aminobenzenesulfonyl azide:

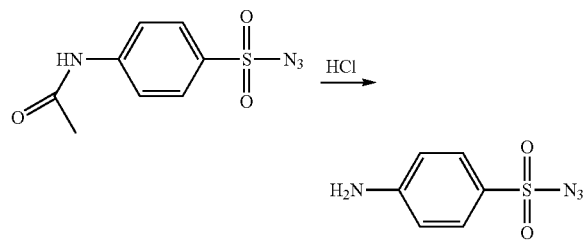

2-oxo-1,3-dioxolan-4-yl)methyl carbonochloridate (0.50 g) was dissolved in 5 ml acetone and was added dropwise to a solution of 0.549 g 4-aminobenzenesulfonyl azide in 5 ml acetone and 0.438 g pyridine at a temperature of 5° C. The dosing time was about 10 minutes. The reaction mixture was stirred for 3 hours at room temperature. After completion of the reaction, the mixture was added to 50 ml cold water, resulting in a white precipitate. The mixture was stirred for 2 hours and the precipitate was washed with water and dried in air, yielding 0.95 g of (2-oxo-1,3-dioxolan-4-yl)methyl (4-azidosulfonyl)phenyl)carbamate as a slightly pink solid:

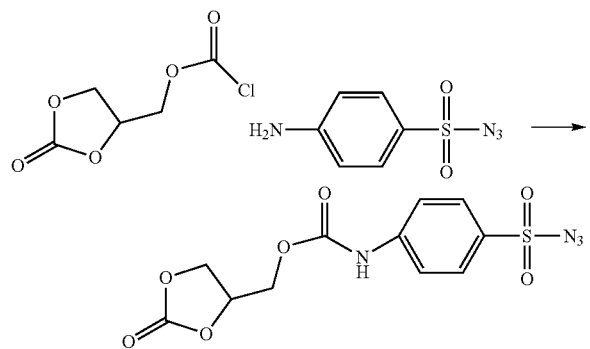

Example 3

Modification of a Polymer 47 grams of emulsion styrene-butadiene rubber (Buna SE1500, eSBR) and 0.93 grams of the (2-oxo-1,3-dioxolan-4-yl)methyl carbonazide of Example 1 were blended on a two-roll mill and intimately mixed. 47.93 grams of this blend were treated in an internal Banbury type mixer at 130-160° C. for the grafting of the azide to the SBR to occur. During this grafting step the temperature of the mixture was allowed to rise to 160° C. in 15 minutes time.

Example 4

Modification of a Polymer 47 grams of solution styrene-butadiene rubber (Buna VSL 4720-0-HN, styrene content 19.5%; vinyl content 47.5%) and 0.94 grams of the (2-oxo-1,3-dioxolan-4-yl)methyl carbonazide of Example 1 were blended on a two-roll mill and intimately mixed. 47.94 grams of this blend were treated in an internal Banbury type mixer at 130° C. for the grafting of the azide onto the SBR to occur. During this grafting step the temperature of the mixture was allowed to rise to 160° C. in 15 minutes time.

Example 5

Modification of a Polymer 47 grams of solution styrene-butadiene rubber (Buna VSL 4526-0 HM styrene content 26%; vinyl content 44.5%) and 0.94 grams of the (2-oxo-1,3-dioxolan-4-yl)methyl carbonazide of Example 1 were blended on a two-roll mill and intimately mixed. 47.94 grams of this blend were treated in an internal Banbury type mixer at 130° C. for the grafting of the azide to the SBR to occur. During this grafting step the temperature of the mixture was allowed to rise to 160° C. in 15 minutes time.

Example 6

Modification of a Polymer 47 grams of solution styrene-butadiene rubber (Buna VSL VP PBR 4045; styrene content 25.7%; vinyl content 22.2%) and 0.94 grams of the (2-oxo-1,3-dioxolan-4-yl)methyl carbonazide of Example 1 were blended on a two-roll mill and intimately mixed. 47.94 grams of this blend were treated in an internal Banbury type mixer at 130° C. for the grafting of the azide to the SBR to occur. During this grafting step the temperature of the mixture was allowed to rise to 160° C. in 15 minutes time.

Example 7

Crosslinking of Modified eSBR Polymer

The modified eSBR rubber of Example 3 was crosslinked using bis(hexamethylene)triamine. This triamine has two primary amine groups and one secondary amine group. Only the two primary amines react with the cyclic carbonate groups of the modified eSBR and form crosslinks.

The amine and the modified rubber were mixed and heated to a temperature of 150° C. to allow crosslinking. The crosslinking was observed using Monsanto rheometer MDR 2000E. Table 1 shows three experiments, with different levels of amine. The crosslink time is displayed as the time required for 90% cure (t90); the crosslink density is displayed as an increase in torque ($\Delta S$), measured by the rheometer.

TABLE 1

| | eSBR | | | |
| --- | --- | --- | --- | --- |
| | unmodified | modified | modified | modified |
| Azide content (phr) | 0 | 2 | 2 | 2 |
| Amine (phr) | 1.15 | 0.57 | 1.15 | 2.30 |
| Molar equivalent | 0.5 | 0.25 | 0.5 | 1 |
| Temperature | 150° C. | 150° C. | 150° C. | 150° C. |
| t90 (min) | 8 | 19 | 17 | 11 |
| $\Delta S$ (Nm) | 0.02 | 0.14 | 0.20 | 0.21 |

The saturation of the $\Delta S$ level to approximately 0.2 Nm indicates that only 0.5 molar equivalents of the amine are required to complete the crosslinking. This means that one mole of the amine reacts with two moles of cyclic carbonate groups. Without modification with azides there is no reactivity towards amines as can be seen in the first entry of Table 1.

Example 8

Crosslinking of Modified sSBR Polymer 47 grams of the modified sSBR rubbers of Examples 4, 5 and 6 were crosslinked at 170° C. using 0.5 molar equivalents (1.15 phr) of bis(hexamethylene)triamine, as found optimal in example 7. The crosslinking was observed using Monsanto rheometer MDR 2000E and the results are displayed in Table 2.

TABLE 2

| sSBR type of Example no. | azide (phr) | t90 (min) | ΔS (Nm) |
|---|---|---|---|
| 4 | 0 | 24 | 0.01 |
| 4 | 2 | 20 | 0.22 |
| 5 | 2 | 20 | 0.19 |
| 6 | 2 | 23 | 0.11 |

All sSBR types show increased torque levels (indicated as ΔS). All sSBR types show crosslinking by amines after modification with (2-oxo-1,3-dioxolan-4-yl)methyl carbonazide. A reference unmodified rubber, here shown for Buna VSL 4720, shows only a negligible increase in ΔS.

Example 9

Filler Rubber Interaction Improvement sSBR Buna VSL 4720-0 HM was modified as described in the example 4, with the additional presence of 1 phr Vulkanox® SKF. The amounts are displayed in Table 3.

TABLE 3

| step 1: modification. | Inv 1 | Comp 1 | Comp 2 |
|---|---|---|---|
| Buna VSL 4720-0-HN | 47 | 47 | 47 |
| cyclic azidoformate | 0.47 | 0 | 0 |
| vulkanox SKF | 0.47 | 0.47 | 0.47 |

From the modified and comparative rubbers, samples were taken and mixed with the components in amounts as mentioned in Table 4 in an internal Banbury type mixer. The silica (Ultrasil™ 7000 GR) was added in two separate portions to the rubber at 80° C. while allowing the temperature to rise to 130° C. for a maximum of 8 minutes. In Comparative experiment 2, Si69 (ex Evonic) was added.

TABLE 4

| step 2: compounding | Inv 1 | Comp 1 | Comp 2 |
|---|---|---|---|
| compound from step 1 (g) | 32 | 32 | 32 |
| Ultrasil 7000 GR (g) | 12.5 | 12.7 | 12.7 |
| treated distillated aromatic extract oil (Vivatec 500) | 3.14 | 3.17 | 3.17 |
| Si69 (g) | 0.00 | 0.00 | 2.15 |

After addition of the silica and other additives to the SBR, a curative package based on sulfur and sulfur accelerators was added to a portion of the silica-filled rubber on a two-rol-mill. The cure pack is displayed in Table 5.

TABLE 5

| step 3: cure pack | Inv 1 | Comp 1 | Comp 2 |
|---|---|---|---|
| compound from step 2 (g) | 42 | 42 | 42 |
| Insoluble sulfur (Crystex ™ HS OT10) (g) | 0.41 | 0.42 | 0.40 |
| n-cyclohexyl-2-benzothialoze sulfeneamide (CBS) (g) | 0.55 | 0.56 | 0.53 |
| diphenyl guanidine (DPG) (g) | 0.00 | 0.00 | 0.67 |
| ZnO (g) | 0.83 | 0.83 | 0.80 |
| Stearic acid (g) | 0.28 | 0.28 | 0.27 |

Table 6 shows the overall recipes.

TABLE 6

| | Inv 1 | Comp 1 | Comp 2 |
|---|---|---|---|
| total recipe (phr) | | | |
| Buna VSL 4720-0-HM | 100 | 100 | 100 |
| (2-oxo-1,3-dioxolan-4-yl)methyl carbonazide | 1 | 0 | 0 |
| vulkanox SKF | 1 | 1 | 1 |
| Silica Ultrasil 7000 | 40 | 40 | 40 |
| TDEA oil | 10 | 10 | 10 |
| Si69 | 0 | 0 | 6.8 |
| Crystex HS OT10 (insoluble sulfur) | 1.5 | 1.5 | 1.5 |
| CBS | 2 | 2 | 2 |
| DPG | 0 | 0 | 2.5 |
| ZnO | 3 | 3 | 3 |
| Stearic acid | 1 | 1 | 1 |

The resulting formulations were compared using the so-called Payne-effect-test, as described in The science and technology of rubber, $3^{rd}$ edition, J. E. Mark, 2005, page 388. This test measures the Payne-effect of a filled system using a dynamic viscoelastic measurement. According to this experiment, a filled SBR rubber sample is subjected to periodic shear strain at 100° C. and 0.7 Hz. The strain is varied from 0.3% to 100%. The measurement is performed on a rubber analyzer, a "Visco Elastograph" ex Gottfert. This test measures the relationship between the sample's elasticity modulus and the subjected strain on the sample and thereby evaluates the interaction between the rubber and the filler by measuring the interaction between the filler particles. The filler-filler interaction is a good indication for the filler-rubber interaction: a high filler-filler interaction indicates a low filler-rubber interaction and vice versa.

Table 7 shows the results of the Payne test on uncured compounds, indicating that comparative experiment 1 shows a high elasticity modulus (G') at low strain values and a fast breakdown to low G' values at high strain. This breakdown indicates the breakdown of the filler network and shows a strong filler-filler interaction and a poor filler-rubber interaction. The experiment according to the invention invention shows a low G' at low strain values and a gradual breakdown at high induced strain to G' values higher than those of comparative experiment 1. This experiment proofs that modification with a cyclic carbonate azide according to the present invention leads to lower filler-filler interaction and higher filler-rubber interaction. This is particularly inferred from the higher modulus values at high strain, which indicate the presence of bound rubber. Bound rubber is a portion of the rubber that is irreversibly bound to the filler particles.

TABLE 7

| strain (%) | elasticity modulus (G') in kPa | |
| --- | --- | --- |
| | invention | comp1 |
| 0.3 | 217 | 606 |
| 0.4 | 227 | 677 |
| 0.6 | 232 | 714 |
| 0.7 | 234 | 731 |
| 1.4 | 234 | 713 |
| 2.8 | 235 | 631 |
| 4.2 | 232 | 530 |
| 5.6 | 230 | 456 |
| 7.0 | 226 | 402 |
| 11.2 | 213 | 289 |
| 14.0 | 203 | 246 |
| 27.9 | 166 | 136 |
| 41.9 | 136 | 101 |
| 55.8 | 114 | 87 |
| 69.8 | 98 | 75 |
| 83.7 | 83 | 65 |
| 100.0 | 71 | 57 |

Because the filler-rubber interaction of the cured compounds are of utmost importance for the ultimate properties of the tire, this interaction has also been evaluated after cure of the compounds at 150° C. (see Table 8). The same conclusions as for the uncured compounds can be drawn: the filler-rubber interaction is much stronger in the case of the azide-modified sSBR according to the present invention.

TABLE 8

| strain (%) | elasticity modulus (G') in kPa | |
| --- | --- | --- |
| | invention | comp1 |
| 0.3 | 691 | 1271 |
| 0.4 | 696 | 1239 |
| 0.6 | 696 | 1211 |
| 0.7 | 695 | 1192 |
| 1.4 | 683 | 1101 |
| 2.8 | 660 | 1032 |
| 4.2 | 645 | 1011 |
| 5.6 | 632 | 989 |
| 7.0 | 620 | 958 |
| 11.2 | 586 | 900 |
| 14.0 | 564 | 850 |
| 27.9 | 487 | 699 |
| 41.9 | 438 | 582 |
| 55.8 | 415 | 502 |
| 69.8 | 385 | |

The better filler-rubber interaction results in a better dispersion of the filler and less filler-filler interaction. This can be observed in Table 9 where the cure data are compared for the compounds from Table 6. These cure data have been recorded using a rubber analyzer, a "Visco Elastograph" ex Gottfert, under conditions (150° C. for 1 hour) sufficient for full crosslinking of the silica-filled SBR compounds.

TABLE 9

| | Inv | Comp 1 |
| --- | --- | --- |
| $M_L$ (Nm) | 0.22 | 0.39 |
| $M_H$ (Nm) | 0.67 | 1.47 |
| $\Delta S$ (Nm) | 0.45 | 1.08 |
| t10 (min) | 4 | 5 |
| t50 (min) | 14 | 12 |
| t90 (min) | 44 | 42 |
| IRHD hardness | 65 | 76 |

The better dispersion of the filler can be observed by the softness of the compound as indicated by the $M_L$ value: the minimum torque measured at the cure temperature and a good indicator of the viscosity of the filled compound. At the same silica content (40 phr), the composition made by the process according to the invention has a lower viscosity than the comparative composition. The higher viscosity of the comparative composition is due to so-called flocculation: agglomeration of the dispersed silica particles. This agglomeration leads to build-up of tough structures, adding to the increased viscosity of the compound, particularly at elevated temperatures. It also adds up to an apparent increase in crosslink density, as indicated by the increased $M_H$ (maximum torque measured in the Visco Elastograph) and $\Delta S$ ($=M_H - M_L$), and leads to hardening of the cured elastomer. This hardening of the rubber after cure is measured by the IRHD hardness (International Rubber Hardness Degrees, ISO 48), which clearly shows the increased hardness for comparative experiment 1 of Table 9. Flocculation further makes processing of the silica compound more difficult, lowers the shelf life of the silica-filled compound, and leads to undesirable and unpredictable mechanical properties of the end product.

The compound prepared in accordance with the present invention has no or only a marginal flocculation due to the improved dispersion of the silica in the rubber, and due to the increased interaction between the rubber and the silica, resulting in a decreased filler-filler interaction.

The invention claimed is:

1. Cyclic carbonate azide having a structure according to the following formula:

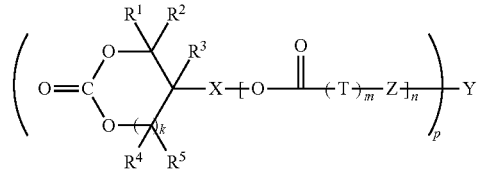

wherein $R^1$-$R^5$ are independently selected from the group consisting of hydrogen, $C_{6-20}$ aryl, $C_{7-36}$ aralkyl, and $C_{1-30}$ alkyl groups; said aryl, aralkyl, and alkyl groups, optionally substituted with heteroatoms, X is a hydrocarbon moiety having at least one carbon atom, T has the structure —N($R^6$)— or —O—, $R^6$ is selected from the group consisting of hydrogen and $C_{1-20}$ alkyl groups, optionally substituted with heteroatoms k is 0, 1, or 2 m is 0 or 1, n is 0 or 1, p is 1 or 2

Z is an aliphatic or aromatic hydrocarbon moiety having at least one carbon atom, optionally substituted with heteroatoms, and Y is either

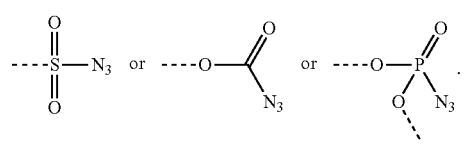

2. Cyclic carbonate azide according to claim 1 wherein T has the structure —N(R$^6$)—.

3. Cyclic carbonate azide according to claim 1 wherein T has the structure —O—.

4. Cyclic carbonate azide according to claim 1 wherein k=0.

5. Cyclic carbonate azide according to claim 1 wherein X is CH$_2$.

6. Cyclic carbonate azide according to claim 1 wherein Z is an aryl group.

7. Cyclic carbonate azide according to claim 1 wherein p=1, n=m=0 and Y is

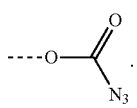

8. Cyclic carbonate azide according to claim 1 wherein p=1, n=m=1, R$^3$ is H, Z is an aryl group, and Y is

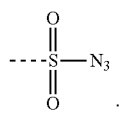

9. Cyclic carbonate azide according to claim 1 wherein p=2, n=m=0, R$^3$ is H, X is CH$_2$, and Y is:

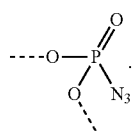

10. Cyclic carbonate azide according to claim 1 wherein k=1.

11. Cyclic carbonate azide according to claim 1 wherein R$^1$, R$^2$, R$^4$, and R$^5$ are hydrogen.

12. Cyclic carbonate azide according to claim 1 wherein R$^3$ is hydrogen or a hydroxy alkyl group.

13. A process for modifying polymers wherein the cyclic carbonate azide according to the following formula:

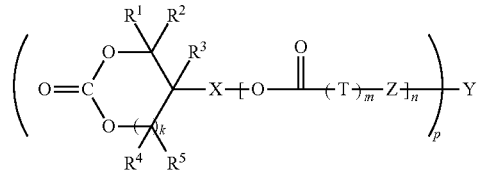

wherein
R$^1$-R$^5$ are independently selected from the group consisting of hydrogen, C$_{6-20}$ aryl, C$_{7-36}$ aralkyl, and C$_{1-30}$ alkyl groups; said aryl, aralkyl, and alkyl groups, optionally substituted with heteroatoms, X is a hydrocarbon moiety having at least one carbon atom, T has the structure —N(R$^6$)— or —O—, R$^6$ is selected from the group consisting of hydrogen and C$_{1-20}$ alkyl groups, optionally substituted with heteroatoms k is 0, 1, or 2 m is 0 or 1, n is 0 or 1, p is 1 or 2

Z is an aliphatic or aromatic hydrocarbon moiety having at least one carbon atom, optionally substituted with heteroatoms, and Y is either

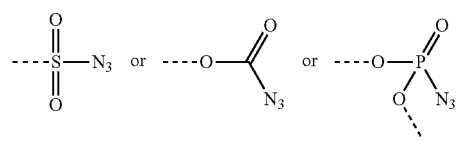

is grafted on said polymer by blending said azide and said polymer and heating the blend at a temperature in the range 100-220° C.

14. Process according to claim 13 wherein the polymer is emulsion-type styrene-butadiene rubber (e-SBR) or solution-type styrene-butadiene rubber (s-SBR).

15. A polymer obtainable by the process of claim 14.

16. A polymer composition comprising the polymer of claim 14 and silica.

17. A method of producing tires comprising the polymer of claim 16.

* * * * *